United States Patent [19]
Baudino et al.

[11] Patent Number: 5,927,277
[45] Date of Patent: *Jul. 27, 1999

[54] METHOD AND APPARATUS FOR SECURING PROBES WITHIN A BURR HOLE

[75] Inventors: Michael D. Baudino, Coon Rapids; Mark T. Rise, Monticello, both of Minn.

[73] Assignee: Medtronic, Inc., Minneapolis, Minn.

[ * ] Notice: This patent is subject to a terminal disclaimer.

[21] Appl. No.: 08/430,967

[22] Filed: Apr. 28, 1995

[51] Int. Cl.⁶ .............................. A61B 5/04; A61N 1/02
[52] U.S. Cl. ...................... 128/642; 607/116; 606/129; 604/175
[58] Field of Search ..................... 128/642, 748; 607/1, 2, 45, 46, 116, 139; 604/175; 606/108, 129, 130

[56] References Cited

U.S. PATENT DOCUMENTS

| | | | |
|---|---|---|---|
| 3,760,811 | 9/1973 | Andrew | 606/180 X |
| 4,328,813 | 5/1982 | Ray . | |
| 4,805,634 | 2/1989 | Ullrich et al. | 128/748 |
| 4,809,694 | 3/1989 | Ferrara | 606/130 |
| 4,955,891 | 9/1990 | Carol | 606/130 |
| 4,998,938 | 3/1991 | Ghajar et al. | 606/130 |
| 5,054,497 | 10/1991 | Kapp et al. | 128/748 |
| 5,464,446 | 11/1995 | Dreessen et al. | 607/116 |

*Primary Examiner*—Jeffrey R. Jastrzab
*Attorney, Agent, or Firm*—Curtis D. Kinghorn; Harold R. Patton

[57] ABSTRACT

An apparatus and method for securing medical devices such as intracerebroventricular and parenchymal catheters and electrical stimulation leads within a cranial burr hole comprising a snap ring assembly selectively secured at the burr hole so that an extension of the assembly, having one or more points of fixation for a catheter or lead, secures a catheter or lead extending through the burr hole at a desired point, thereby minimizing undesirable movement of the positioned medical device. The catheter or lead is secured by opposed edges of bar extensions that are placed about the lead or catheter when the snap ring assembly is squeezed and a space between the edges is opened, but that close upon and hold the catheter or lead when the snap ring is released; by a scissors-like jaws mechanism operatively coupled to the snap ring assembly which clamps and holds the positioned device; or by a rigid extension having at least one fixation point through which the catheter or lead passes and at which the catheter or lead is secured.

28 Claims, 6 Drawing Sheets

METHOD AND APPARATUS FOR SECURING PROBES WITHIN A BURR HOLE

BACKGROUND

The present invention relates generally to methods and apparatus for securing medical devices such as intracerebroventricular catheters, parenchymal catheters or electrical stimulation leads within a cranial burr hole.

Medical procedures involving access to the brain through a burr hole in the skull are under increasing use. Three such procedures are electrical stimulation of the brain for such purposes as relief of chronic pain and treatment of movement disorders, and the use of parenchymal or intracerebroventricular catheters for infusing pharmaceutical agents. A typical electrical brain stimulation system comprises a pulse generator operatively connected to the brain by a lead having at its distal end an electrode designed to be implanted within the brain, and having at its proximal end a connector assembly designed to connect to the pulse generator. Use of a parenchymal catheter generally involves the insertion of a catheter within the brain to dispense pharmaceutical agents at a specific desired location. The locations include the ventricular spaces of the brain.

One critical aspect of the above-listed procedures, and of any other such procedures that involve instrument access to the brain through a burr hole, is the precision with which any such inserted devices, e.g. catheters and leads, are placed. Once a satisfactory burr hole is established at a particular site, to avoid unintended injury to the brain, physicians typically use stereotactic procedures to position the inserted devices. One stereotactic instrument which may be used, for example, to position a lead electrode is disclosed in U.S. Pat. No. 4,350,159 to Gouda, incorporated herein by reference. As can be appreciated, once an inserted device is properly positioned, it is important that the device not be moved. Even one millimeter of travel of the positioned device may cause unsatisfactory results or, in some cases, severe injury to the brain. Accordingly, reliable methods and apparatus for fixing the positioned device at the burr hole are necessary.

Previous designs of systems for securing a positioned device within a burr hole have a number of drawbacks. U.S. Pat. No. 4,328,813 to Ray, incorporated herein by reference, discloses a socket and cap arrangement in which the cap was positioned so as to trap a positioned electrical stimulation lead between the socket and cap by friction. That arrangement involved securing the lead off center from the burr hole in a manner such that during installation of the anchoring cap a stereotactic instrument could not be used to support the lead. Often the lead needed to be manually supported in place while the anchoring cap was being installed. The lead thus was susceptible to inadvertent movement by the physician during the cap installation period. Further, in the interaction of the cap and socket the lip of the cap tended to pull on the lead and to cause its dislodgement.

SUMMARY OF THE INVENTION

As explained in more detail below, the present invention overcomes the above-noted and other shortcomings of prior burr hole anchoring devices and methods.

As used herein, the term "positioned device" refers to any elongated medical apparatus having at least proximal and distal ends: 1) that extends through a burr hole, and 2) that is to be anchored relative to a known location within the burr hole, so that the location of the distal end of the apparatus at, near, or within the area to be treated may be controlled. Where a positioned device is either an electrical stimulation lead or catheter extending through a cranial burr hole, the distal end of the positioned device typically will be situated within the brain or brain ventricles, and the desired control of that end will be holding the distal end as stationary as possible. Although that preferred embodiment of the present invention is the one described herein, it should be readily apparent to one of ordinary skill in the art having the benefit of this disclosure that the present invention is not necessarily so limited.

The present invention preferably comprises an apparatus and method of fixing a positioned device such as a lead or catheter at a cranial burr hole. The invention has the advantages that it allows anchoring to occur before the lead or catheter is detached from the stereotactic apparatus, thereby reducing the possibility of movement. Moreover, the lead or catheter can be fixed at any point that it may pass through the burr hole, but still keep access to the surface of the brain open.

Three separate embodiments of the present invention are described herein, each generally using at least one extension having an anchoring or gripping portion means extending within the circle formed by the burr hole cap. The extension having a gripping portion may be formed integrally with the burr hole ring. Alternatively, in the most preferred embodiments, the extension will be a portion of a snap ring which can be selectively secured within the burr hole cap. The burr hole cap may be configured to accept multiple snap ring assemblies. Such multiple snap ring assemblies allow for fixation of more than one lead, catheter or other device in a single burr hole, if desired. In one preferred embodiment, the portion for anchoring or gripping the lead or catheter comprises a rigid bar lying along a radius of the circle formed by the ring. The rigid bar has points of fixation along its length, permitting fixation at any point along the radial axis of the burr hole. The snap ring can be rotated so that the bar coincides with any particular radius of the burr hole, so that a catheter or lead may be fixed in place at virtually any location within the burr hole. This avoids having to deflect the catheter or lead in a manner which could affect the placement of the distal end within the brain.

The exemplary embodiments of the present invention described herein differ by the method with which the catheter or lead is attached for anchoring. In the first, the bar comprises two parts that slide open when the snap ring is spread apart, allowing the ring to be placed around a positioned device. However, when the ring is squeezed to a smaller diameter until it fits within the pre-positioned burr ring, the parts can be passed around the catheter or lead so that when the snap ring is released toward a natural state, the parts squeeze together to position the lead at some known location along the length of the parts, fixing the positioned device in place. In the second embodiment, the bar comprises a scissors-like jaws mechanism having at least two parts. The snap ring is positioned about a catheter or lead so that the jaws may be closed to hold the catheter or lead in place. In the third embodiment, the bar comprises a rigid extension with multiple spaced holes through which the catheter or lead passes. The catheter or lead when satisfactorily positioned is fixed to the extension and held in place with an adhesive, a grommet, friction (e.g. a force fit in the case of a tapered catheter) or other suitable means. However, the third embodiment differs from the first two embodiments in that it will typically require the rigid extension to be in place before the catheter or lead is passed through and positioned.

Examples of the more important features of this invention have been broadly outlined above in order that the detailed description that follows may be better understood and so that contributions which this invention provides to the art may be better appreciated. There are, of course, additional features of the invention which will be described herein and which will be included within the subject matter of the claims appended hereto.

DETAILED DESCRIPTION OF THE INVENTION

Retention assemblies in accordance with the present invention can be placed directly within a burr hole or within a pre-positioned burr hole ring. Whether a separate burr hole ring is used with a particular patient will depend on the specific circumstances involved in that patient's case. Further, as one might imagine, there are many possible sizes and shapes of burr hole rings. The selection of one burr hole ring over another will depend on numerous factors such as the size or shape of the burr hole, whether there is a need to hold multiple snap rings, etc. Thus, it should be understood that the following description, by way of example, shows exemplary burr hole ring configurations which may be used in connection with the present invention. Additionally, as noted previously herein, the device retaining mechanism may be formed as an integral portion of the burr hole ring, or it may be formed as a part of a separate member selectively attachable to the burr hole ring. Such a separate burr hole ring would typically be pre-placed within the burr hole, with the retention mechanism carrying member insertable into the pre-placed burr hole ring. The exemplary configurations of retaining mechanisms disclosed herein are depicted as snap rings which would be independently engageable with a burr hole ring assembly. It should be already understood, however, that each of the disclosed retaining mechanisms may be integrally formed with the burr hole ring.

Figure 1:
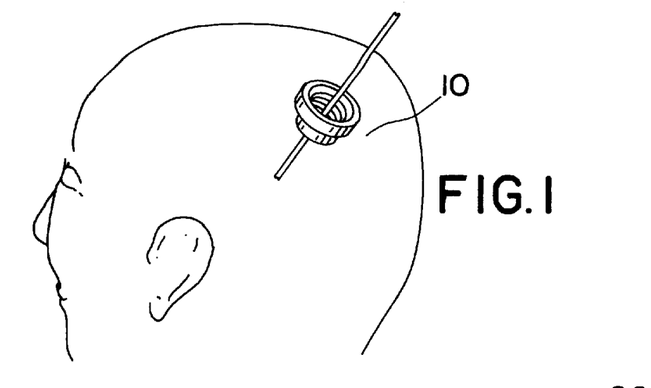
FIG. 1 is an illustration of a exemplary burr hole ring/snap ring assembly in accordance with the present invention.
Figures 2, 3, 4:
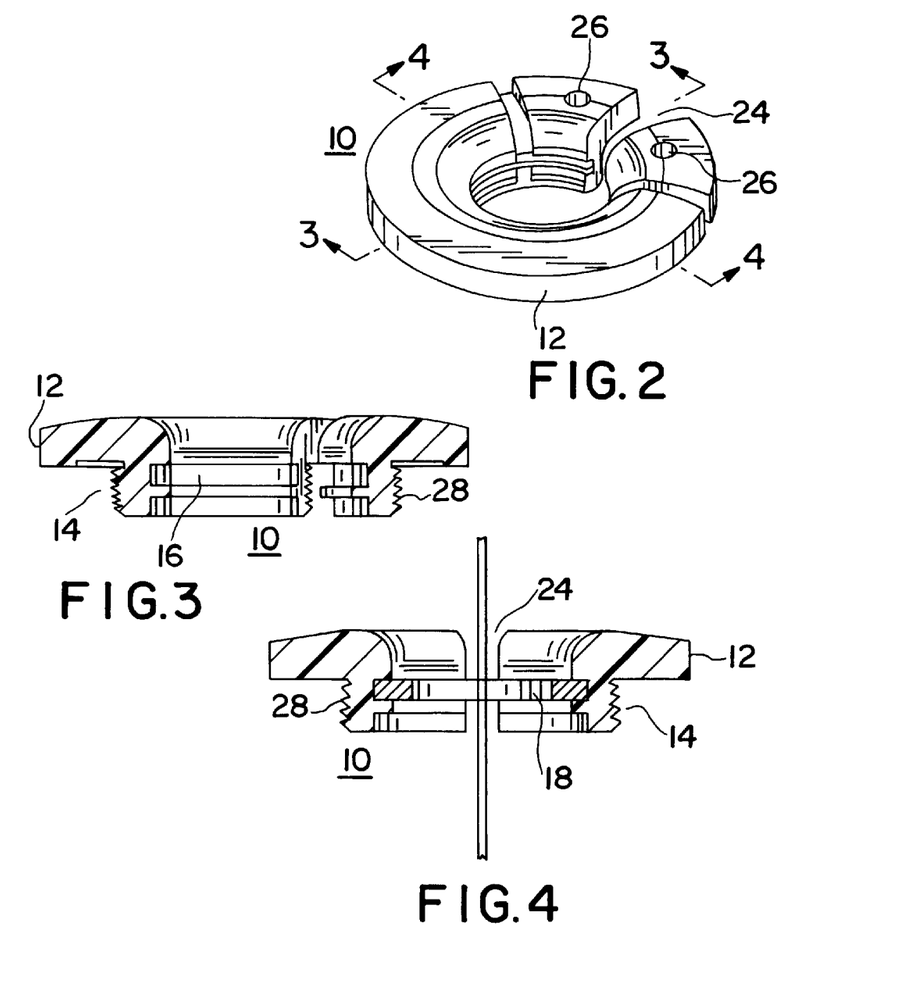
FIG. 2 is an illustration of an exemplary burr hole ring assembly in accordance with the present invention.
FIG. 3 is a cross-sectional view of the exemplary burr hole ring assembly shown in FIG. 2, taken along the line 3—3 in FIG. 2.
FIG. 4 is a cross-sectional view of the exemplary burr hole ring assembly shown in FIG. 2, taken along the line 4—4 in FIG. 2, also showing in cross-section an exemplary snap ring assembly positioned within the burr hole ring assembly and holding a positioned device.
Figure 4A:
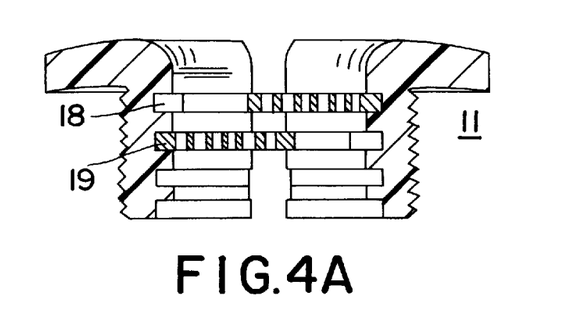
FIG. 4A is a cross-sectional view of an exemplary burr hole ring assembly in accordance with the present invention, also showing in cross-section multiple exemplary snap ring assemblies positioned within the burr hole ring assembly.

Burr hole ring 10, shown in FIGS. 1–4, is a burr hole ring comprising an upper flange portion 12, lower portion 14, and a receiver for receiving a snap ring. As shown in FIG. 3, lower portion 14 has a snap ring receiver comprising a C-clip slot 16. C-clip slot 16 is configured to receive snap ring assemblies such as the ones described herein. Preferably, a snap ring released to assume its natural state will fit snugly within C-clip slot 16 so that no movement of the released snap ring relative to the burr hole ring 10 will occur. C-clip slot 16 further need not be located within the lower portion 14 of burr hole ring 10. Both the upper and lower portions 12,14 of burr hole ring 10 may have one or more of such slots or other snap ring receiving means. FIG. 4 shows a snap ring 18 positioned within a C-clip slot 16 in the lower portion 14 of burr hole ring 10. FIG. 4A shows an exemplary burr hole ring 11 having multiple snap ring receivers comprising C-clip slots, with snap rings 18,19 positioned within the two uppermost slots.

In the depicted exemplary embodiment, burr hole ring 10 is itself a type of snap ring. Burr hole ring 10 is a generally annular member, having a radial gap or opening 24, and holes or pockets 26 adapted to receive forceps or another suitable device for squeezing burr hole ring 10 to a diameter slightly smaller than the nominal diameter of the burr hole ring when it is in a natural state. It is this squeezing or compression which permits placement of the burr hole ring within a burr hole, and the subsequent expansion which secures burr hole ring 10 within the burr hole. Preferably, ridges or threads 28 situated at the outside diameter of lower portion 14 mechanically engage the skull within the burr hole, or engage another ring previously placed at the burr hole, and assist in preventing dislodgement of burr hole ring 10.

As noted earlier, use of a separate burr hole ring is optional depending upon the particular circumstances involved in a particular case. Thus, a probe anchoring assembly in accordance with the present invention may comprise a snap ring adapted with an upper flange portion, a lower burr hole engaging portion, or both; and an anchoring or gripping means coupled to the snap ring for fixing a probe in place.

An exemplary embodiment of a snap ring 34 in accordance with the present invention is shown in FIGS. 5–8.

Snap ring 34 is configured with a lead retaining mechanism including at least two arms 36,38 extending generally toward the center of the snap ring 34. The arms 36,38 are preferably rigid bars adapted for engaging the lead 32 at any one of a plurality of positions along the lengths of the arms, with beach arm preferably equipped with opposed serrated edges or teeth 37,39 for grasping or holding the lead 32, as shown in FIG. 7.

Figures 5, 6, 7:
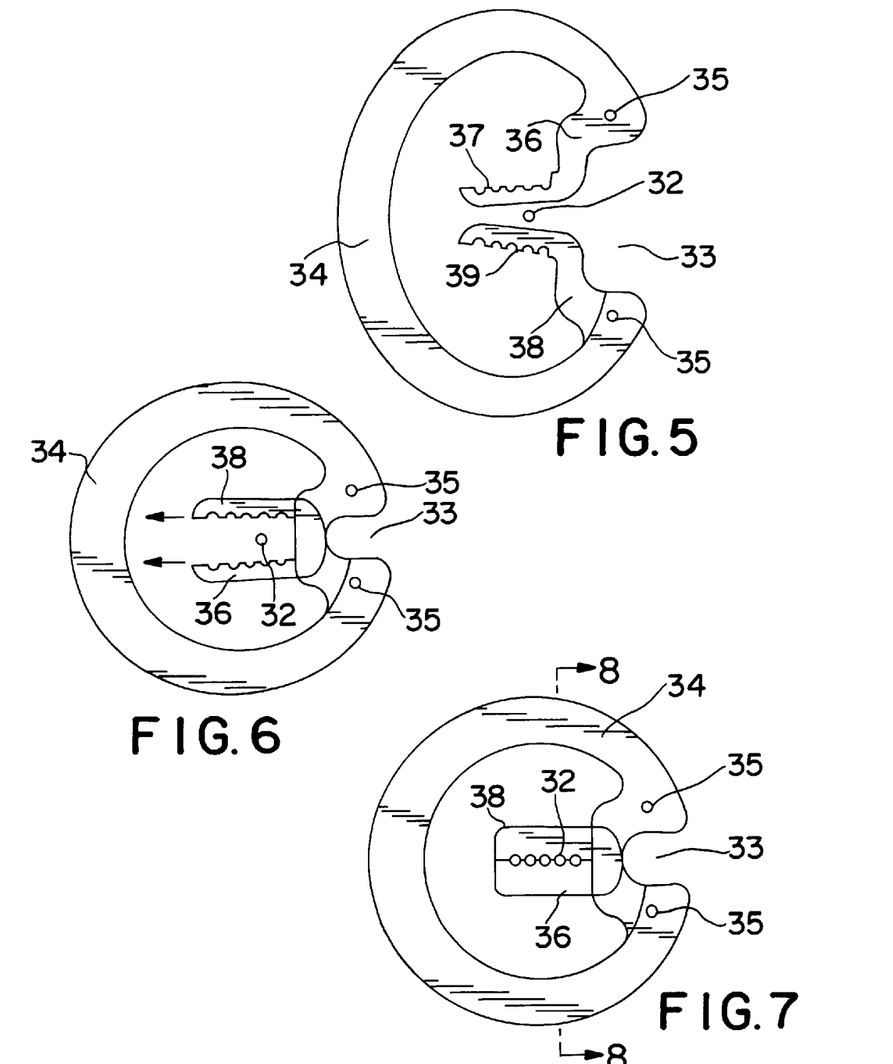
FIG. 5 is an illustration of an exemplary snap ring assembly in accordance with the present invention, depicted in a top view as being open for placement about a wire lead.
FIG. 6 is an illustration of an exemplary snap ring assembly in accordance with the present invention, depicted in a top view about a wire lead prior to anchoring.
FIG. 7 is an illustration of an exemplary snap ring assembly in accordance with the present invention, depicted in a top view as anchoring in place a wire lead.
Figure 8:
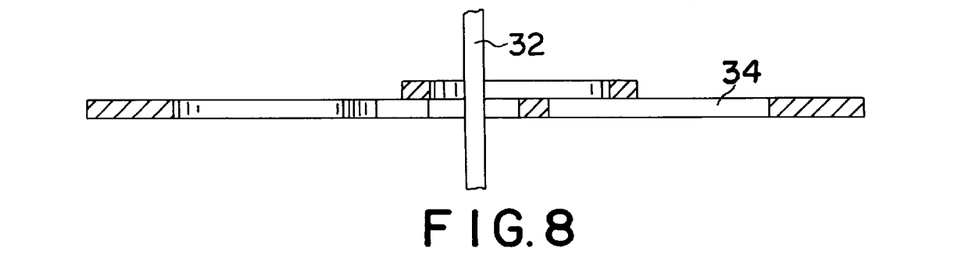
FIG. 8 is a cross-sectional view of the exemplary snap ring assembly of FIG. 7, taken along the line 8—8 in FIG. 7.
Figure 9:
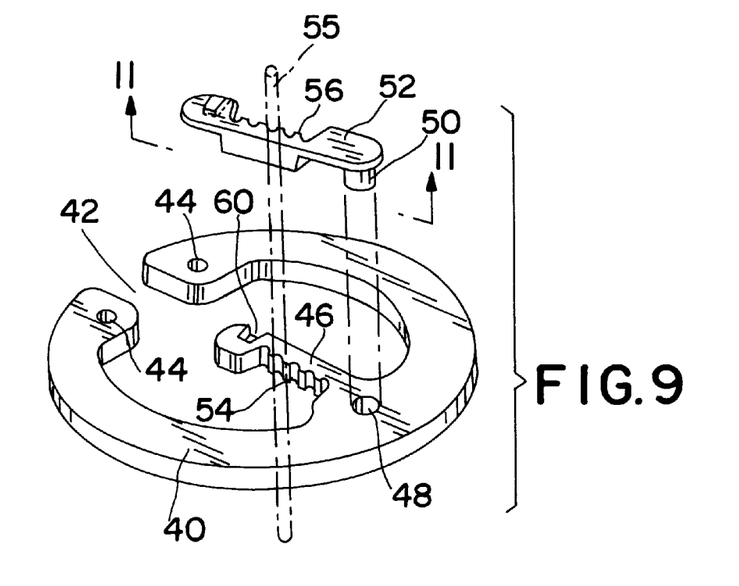
FIG. 9 is an illustration of an exemplary snap ring assembly in accordance with the present invention, depicted in a three-dimensional exploded view from above, as anchoring in place a wire lead or catheter.
Figure 10:
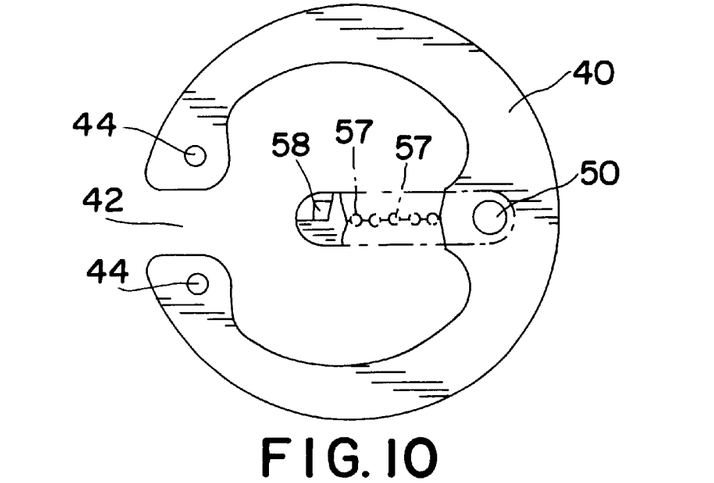
FIG. 10 is an illustration of the snap ring assembly shown in FIG. 9, depicted in a view from below.
Figure 11:
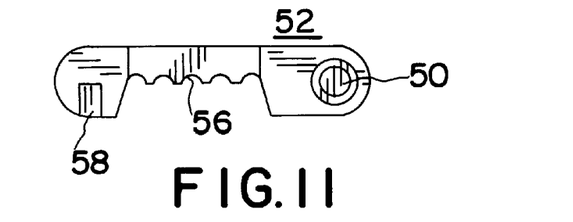
FIG. 11 is a view of the snap ring assembly shown in FIG. 9, taken along the line 11—11 in FIG. 9.
Figure 12:
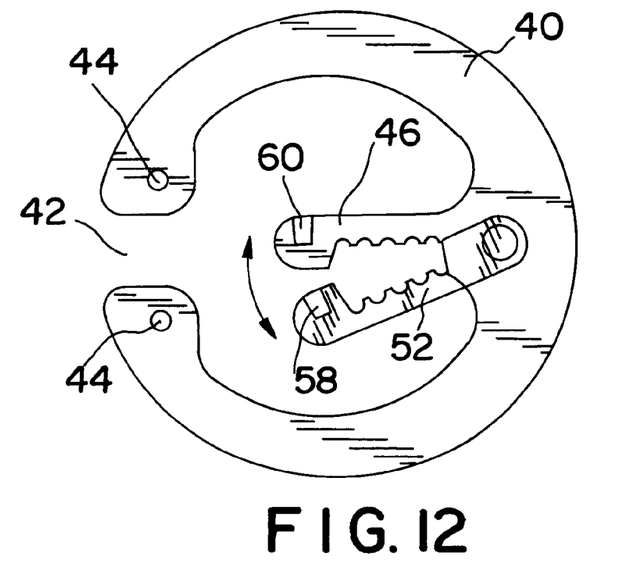
FIG. 12 is an illustration of the snap ring assembly shown in FIG. 9, depicted in a top view and showing the movement of the scissors-like jaws.

Holes or pockets 35, preferably located as shown near the opening 33 of the snap ring 34, are configured to receive forceps or another suitable device for spreading open the snap ring so that it can be placed about the lead 2 (see FIG. 5). When in place about lead 32, the snap ring 34 then is squeezed together to create, i.e. open, a space between the opposed edges 37,39 for receiving lead 32 (see FIG. 6). The squeezing of snap ring 34, in addition, reduces slightly its diameter, allowing snap ring 34 to be rotated and placed at a desired orientation within a pre-positioned burr hole ring. Once snap ring 34 is suitably situated within the previously placed burr hole ring, the anchoring of lead 32 is accomplished by allowing snap ring 34 to assume its natural state, i.e. a condition in which snap ring 34 is neither spread open nor squeezed smaller significantly. Under such circumstances, serrated edges 37,39 clamp about lead 32, holding it in place. Once the lead is secured in place within the area inside burr hole ring 10, a flexible cap or plug may be installed to engage burr hole ring 10 to mechanically isolate the aperture and the exposed tissue. Typically, the cap will be a silicon elastomer member configured to engage burr hole ring 10. The lead (or other device) will typically be bent to the side. Because of the securing of the lead at a location within the burr hole ring, any tendency of the distal portion of the lead to change in position in response to this bending is minimized.

Another exemplary embodiment of the present invention is shown in FIGS. 9–12. A snap ring 40 having an opening 42 is again configured with holes or pockets 44 for receiving a compressing tool to place the snap ring within a previously positioned burr hole ring. In this embodiment, the mechanism for anchoring a lead, catheter, or other positioned device includes a first rigid bar 46 extending from snap ring 40 to within the circle formed by the snap ring; and a second rigid bar 52 pivotally coupled to snap ring 40 so that rigid bars 46 and 52 form a scissors-like pair of jaws.

As shown in the drawings, the pivotal coupling preferably comprises a post 50 extending from a proximate first end of second rigid bar 52, and a socket 48 disposed in snap ring 40 near the point where rigid bar 46 joins snap ring 40. Socket 48 is adapted to receive post 50, permitting rigid bar 52 to rotate about socket 48. (See FIG. 12). Post 50 may be secured within socket 48 by deformation, to operatively couple rigid bars 46 and 52 together. Fixation points extend along the length of rigid bars 46, 52. In this embodiment, bars 46, 52 will preferably have oppositely opposed serrated edges 54, 56 which meet upon the rotation of bar 52 into bar 46 and together form a plurality of holes 57 for receiving a lead or catheter 55. The dimensions and configuration of serrated edges 54, 56 may be selected in reference to the size of the lead, catheter or other device being retained. A tab 58 preferably extends from the second end of bar 52, and a hole 61 in bar 46 is adapted to receive tab 58 by an interference fit, so that when a positioned device is clamped between bars 46 and 52 the insertion of tab 58 into hole 61 comprises a locking mechanism securing the two bars together and preventing movement of bar 52 from about the positioned device.

Figure 13:
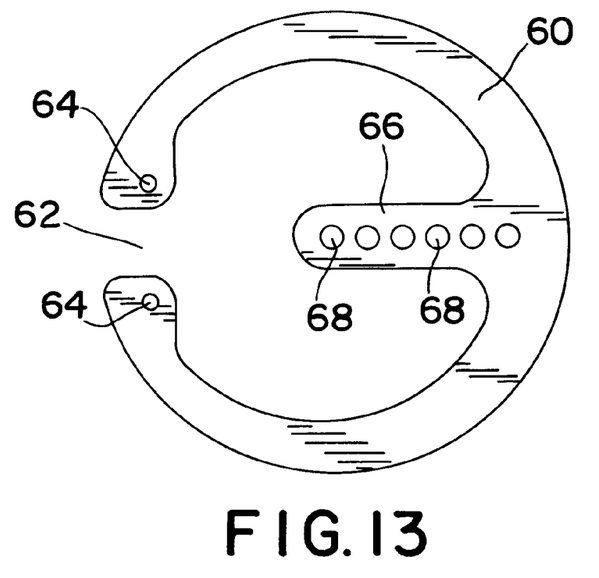
FIG. 13 an illustration of an exemplary snap ring assembly in accordance with the present invention.

Yet another exemplary embodiment of the present invention is shown in FIG. 13. A snap ring 60 having an opening 62 is adapted with holes or pockets 64 for receiving a device for spreading open the snap ring. At least one rigid bar 66 extends from snap ring 60 to within the circle formed by the ring. A plurality of holes 68 are located within bar 66. The holes 68 are adapted to receive the catheter or lead to be placed. With this embodiment, the catheter or lead must be placed through one of the holes 68 prior to the positioning of the catheter 24 within the cranium as described above. Selection of an appropriate hole 68 to receive the catheter or lead will depend upon the desired placement of the catheter or lead within the burr hole. The size and positioning of the holes may be selected in reference to the particular application, as may the size and shape of the bar itself. The orientation of the holes may be selected to facilitate optimal "coverage" of the dimension within the ring, through rotation. This can be generally determined through use of the stereotactic instrument. It is contemplated, therefore, that due to the shape of rigid bar 66, the number of holes positioned within the bar, and the physician's ability to rotate the snap ring/bar assembly in placing it within a patient's skull (or a burr ring or snap ring), it will be possible to secure the catheter or lead at virtually any desired location within the burr hole. Once the catheter or lead is satisfactorily positioned, more permanent fixation can be accomplished through the use of an adhesive, a grommet, frictional forces, or other suitable means.

Figure 14A:
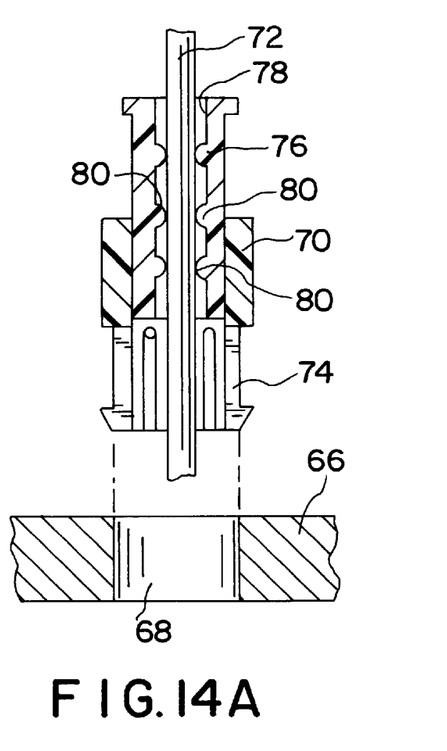
FIG. 14A is a cross-sectional view of an exemplary snap ring assembly latching means for holding in place a wire lead or catheter in accordance with the present invention.
Figure 14B:
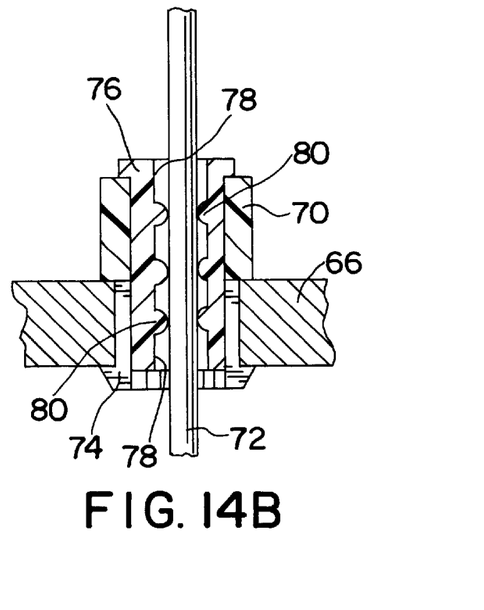
FIG. 14B is an illustration of the snap ring assembly latching means shown in FIG. 14A, as fixing and holding a catheter in accordance with the present invention.

One such suitable means for fixing a catheter or lead to the rigid bar 66 of snap ring 60 is shown in FIGS. 14A–B. An elongated, generally tubular outer carrier 70 is adapted on one end with means for engaging the bar 66 at the hole 68 selected to receive the catheter 72 to be positioned. Preferably, the engaging means comprises a split, flanged collet 74 that locks within hole 68. When an inner carrier 76 positioned about catheter 72 is placed within outer carrier 70 prior to locking, the subsequent locking of the assembly within the hole 68 creates a frictional or interference fit between the catheter 72 and inner carrier 76; between the inner carrier 76 and the outer carrier 70; and between the outer carrier 70 and the extension 66, so that no substantial rotational or translational movement of the catheter 72 within the hole 68 may occur. As shown in FIGS. 14A–B, depending upon the size of the catheter, to achieve a sufficient fit between the catheter 72 and inner carrier 76, the inner surface 78 of inner carrier 76 may be adapted with one or more ridges 80. The ridges 80 preferably are integrally formed with the inner carrier 76, and made of a deformable, soft polymer such as polyurethane. Of course, rings or seals also may be used within the annular space between the catheter 72 and inner carrier 76 to help hold a catheter or wire lead in place. Again, the primary consideration is that upon the latching assembly being locked in place (see FIG. 14B) no undesirable movement of the catheter or lead may occur.

Figure 15A:
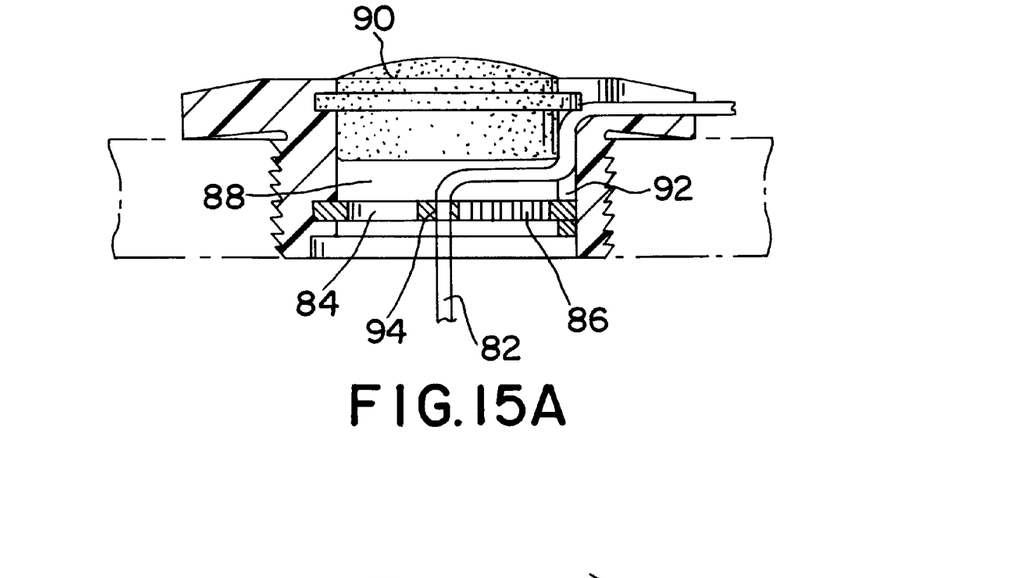
FIG. 15A is an illustration of an exemplary burr hole ring/snap ring assembly, depicted in a cross-sectional view, as the snap ring assembly shown in FIG. 13 within an exemplary burr hole ring, holding a wire lead, in accordance with the present invention.
Figure 15B:
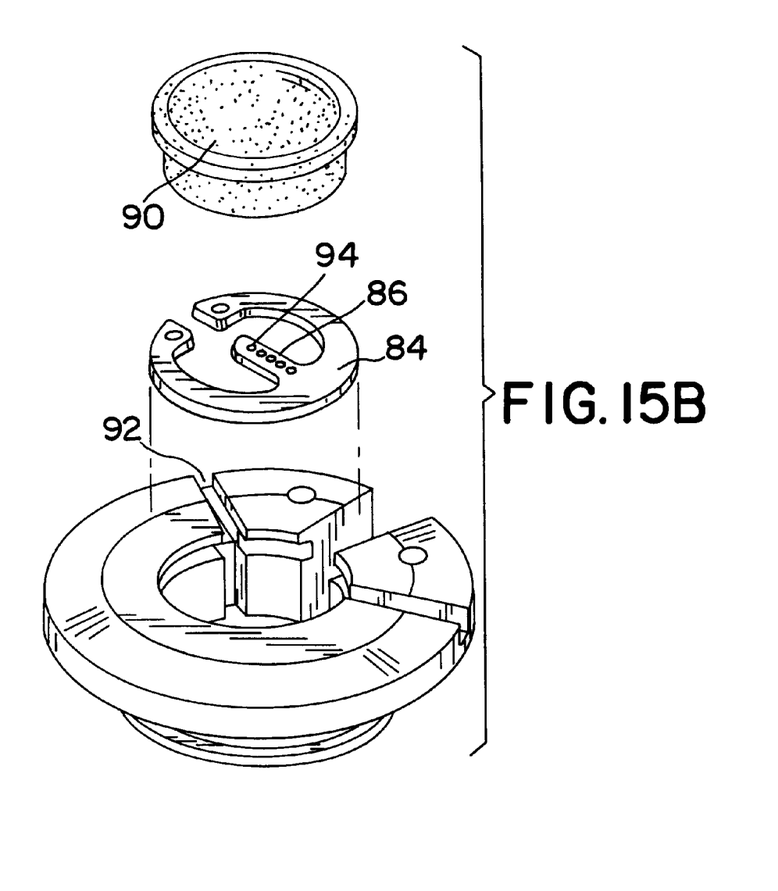
FIG. 15B is an illustration of the burr hole ring/snap ring assembly shown in FIG. 15A, depicted in a three-dimensional exploded view.

FIGS. 15A–B illustrate a modified burr ring/snap ring assembly in accordance with the present invention as holding in place a wire lead 82. A snap ring 84 (of the type depicted in FIG. 13) is housed within the receiving slot of a modified burr ring. The wire lead 82 secured at a desired location 94 to extension 86 passes through the chamber 88 located beneath septum 90 and is situated within a channel 92 formed in the modified burr ring. Because of the securing of the wire lead at the point 94 within the burr hole ring, any tendency of the distal portion of the lead situated within the patient's body to change in response to bending of the proximate end of the wire lead is minimized.

There are a variety of materials which can be used to construct the snap rings and burr hole rings discussed herein.

Preferably, the components are made of a durable, lightweight metals or polymers. Examples of materials which might be used to construct the components disclosed herein include one or more of the following, either alone or in combination: metals, such as stainless steel, titanium, or other biocompatible alloys; and polymers, such as polyurethane (e.g. 75D), polysulfone, or nylon. The burr hole plug preferably would be made of a softer polymer such as polyurethane (e.g. 80A) or silicone. Of course, there are numerous options available for materials, and those listed above should be considered only as examples of materials which might be used. The selection of suitable materials will depend upon the circumstances surrounding the particular application involved.

Although the preferred embodiment of this invention has been described hereinabove in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. A mounting assembly for retaining a probe through a burr hole in a patient's skull in a desired fixed relation relative to the skull, comprising:
    a burr hole ring configured to be mechanically coupled to the skull proximate the burr hole; and
    an engaging member coupled to the burr hole ring, the engaging member having a plurality of apertures to receive and position the probe relative to the burr hole ring.

2. The mounting assembly of claim 1, wherein the engaging member is detachably coupled to the burr hole ring.

3. The mounting assembly of claim 1, wherein the engaging member includes a clamping assembly having a first open position and a second closed position.

4. A mounting assembly for retaining a probe extending through a burr hole in a patient's skull, comprising:
    a burr hole ring configured to be mechanically coupled to the skull proximate the burr hole; and
    an engaging member coupled to the burr hole ring, the engaging member having a plurality of apertures through which the probe may selectively be extended so that the probe may be locatable at a plurality of sites within the burr hole.

5. A mounting assembly for retaining a device through a burr hole in a patient's skull in a generally fixed position, comprising:
    a burr hole ring assembly, comprising:
        a generally annular portion having a surface configured to engage the patient's skull, the generally annular portion defining a central aperture;
        a retaining mechanism extending from the annular portion into the central aperture, the retaining mechanism having a plurality of positioning apertures to receive and position the device relative to the generally annular portion, the retaining mechanism having means to selectively engage the device at one of the plurality of positioning apertures within the central aperture.

6. The mounting assembly of claim 5, wherein the retaining mechanism is a discrete member from the annular portion.

7. A method for securing a device at a desired orientation within a burr hole, comprising:
    placing the device through the burr hole;
    positioning the device within the burr hole so that the device assumes the desired orientation;
    placing a snap ring assembly about the positioned device, the snap ring assembly comprising anchoring means adapted to hold the positioned device and means for securing the snap ring assembly at the burr hole;
    aligning the snap ring assembly at the burr hole so that when the snap ring assembly is secured at the burr hole the anchoring means can hold the positioned device;
    securing the aligned snap ring assembly at the burr hole; and
    engaging the anchoring means to hold the positioned device.

8. The method of claim 7, wherein the step of engaging the anchoring means includes the step of engaging the anchoring means to hold the positioned catheter as the aligned snap ring assembly is secured at the burr hole.

9. A method for securing a probe within a burr hole of a patient, comprising the steps of:
    placing a burr hole ring within the burr hole;
    providing a securing member, the securing member selectively engageable with the probe and the burr hole ring, the securing member having a plurality of positioning apertures to receive and position the device relative to the securing member;
    placing the probe at a desired orientation within the burr hole;
    engaging the securing member with the probe and the burr hole ring to secure the probe to the burr hole ring.

10. The method of claim 9, wherein the step of providing a securing member includes the step of providing a securing member that is a snap ring selectively engageable with the burr hole ring.

11. The method of claim 9, wherein the step of providing a securing member includes the step of providing a securing member that is releasably engageable with the probe.

12. The method of claim 9, wherein the step of placing the probe includes the step of placing a probe that is a catheter.

13. The method of claim 9, wherein the step of placing the probe includes the step of placing a probe that is an electrode.

14. A method for securing a device at a desired orientation within a burr hole, comprising:
    placing a snap ring assembly about the device, the snap ring assembly having anchoring means to hold the device at the desired orientation, the snap ring assembly also having means for securing the snap ring assembly at the burr hole;
    placing the device through the burr hole;
    positioning the device within the burr hole so that the assumes the desired orientation;
    aligning the snap ring assembly at the burr hole so that when the snap ring assembly is secured at the burr hole, the anchoring means can hold the positioned device;
    securing the aligned snap ring assembly at the burr hole; and
    engaging the anchoring means to hold the positioned device.

15. The method of claim 14, wherein the step of placing a snap ring assembly includes placing a snap ring assembly wherein the anchoring means comprises a pair of cooperatively engageable jaws configured to engage the catheter.

16. The method of claim 15, wherein the step of placing a snap ring assembly includes placing a snap ring assembly wherein the jaws are pivotally coupled to one another.

17. A mounting assembly for retaining a probe through a burr hole in a patient's skull in a desired fixed relation relative to the skull, comprising:

a burr hole ring configured to be mechanically coupled to the skull proximate the burr hole; and an engaging member coupled to the burr hole ring, the engaging member having a clamping assembly having two arms pivotally connected to receive and position the probe between the arms relative to the burr hole ring.

18. The mounting assembly of claim 17, wherein the engaging member is detachably coupled to the burr hole ring.

19. A mounting assembly for retaining a probe extending through a burr hole in a patient's skull, comprising:

a burr hole ring configured to be mechanically coupled to the skull proximate the burr hole; and an engaging member coupled to the burr hole ring, the engaging member having a clamping assembly having two arms pivotally connected to receive and position the probe between the arms relative to the burr hole ring, the arms forming at least one aperture through which the probe may selectively be extended so that the probe may be locatable at a plurality of sites within the burr hole.

20. A mounting assembly for retaining a device through a burr hole in a patient's skull in a generally fixed position, comprising:

a burr hole ring assembly, comprising:

a generally annular portion having a surface configured to engage the patient's skull, the generally annular portion defining a central aperture;

a retaining mechanism extending from the annular portion into the central aperture, the retaining mechanism having a clamping assembly having two arms pivotally connected to receive and position the probe between the arms relative to the burr hole ring.

21. The mounting assembly of claim 20 wherein the arms form at least one aperture through which the probe may selectively be extended so that the probe may be locatable at a plurality of sites within the central aperture.

22. The mounting assembly of claim 20, wherein the retaining mechanism is a discrete member from the annular portion.

23. A method for securing a device at a desired orientation within a burr hole, comprising:

placing the device through the burr hole;

positioning the device within the burr hole so that the device assumes the desired orientation;

placing a snap ring assembly about the positioned device, the snap ring assembly including anchoring means having a clamping assembly having two arms pivotally connected to receive and position the probe between the arms relative to the burr hole ring and means for securing the snap ring assembly at the burr hole;

aligning the snap ring assembly at the burr hole so that when the snap ring assembly is secured at the burr hole the anchoring means holds the positioned device;

securing the aligned snap ring assembly at the burr hole; and engaging the anchoring means to hold the positioned device.

24. The method of claim 23 wherein the step of engaging the anchoring means includes the step of engaging the anchoring means to hold the positioned catheter as the aligned snap ring assembly is secured at the burr hole.

25. A method for securing a probe within a burr hole of a patient, comprising the steps of:

placing a burr hole ring within the burr hole;

providing a securing member, the securing member selectively engageable with the probe and the burr hole ring, the securing member having a clamping assembly having two arms pivotally connected to receive and position the probe between the arms relative to the burr hole ring;

placing the probe at a desired orientation within the burr hole;

engaging the clamping mechanism to receive and position the probe between the arms;

engaging the securing member with the probe and the burr hole ring to secure the probe to the burr hole ring.

26. The method of claim 25, wherein the step of providing a securing member includes the step of providing a securing member that is a snap ring selectively engageable with the burr hole ring.

27. The method of claim 25, wherein the step of placing the probe includes the step of placing a probe that is a catheter.

28. The method of claim 25, wherein the step of placing the probe includes the step of placing a probe that is an electrode.

* * * * *

UNITED STATES PATENT AND TRADEMARK OFFICE
CERTIFICATE OF CORRECTION

PATENT NO. : 5,927,277
DATED : July 27, 1999
INVENTOR(S) : Mark T. Rise
                Michael D. Baudino It is certified that error appears in the above-identified patent and that said Letters Patent is hereby corrected as shown below:

Column 8, Line 58: "hole so that the assumes" should be "hole so that the device assumes"

Signed and Sealed this

Third Day of October, 2000

Attest:

Q. TODD DICKINSON

Attesting Officer          *Director of Patents and Trademarks*